(12) United States Patent
Katoh et al.

(10) Patent No.: US 7,481,742 B2
(45) Date of Patent: Jan. 27, 2009

(54) WALKING ASSISTANCE DEVICE

(75) Inventors: Hisashi Katoh, Wako (JP); Takashi Hirata, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 10/557,732

(22) PCT Filed: Mar. 15, 2004

(86) PCT No.: PCT/JP2004/003404

§ 371 (c)(1),
(2), (4) Date: Jun. 23, 2006

(87) PCT Pub. No.: WO2004/103247

PCT Pub. Date: Dec. 2, 2004

(65) Prior Publication Data

US 2007/0010378 A1    Jan. 11, 2007

(30) Foreign Application Priority Data

May 21, 2003    (JP) .............................. 2003-143500

(51) Int. Cl.
*A63B 22/00*    (2006.01)
*A61H 1/02*    (2006.01)
*A61F 5/00*    (2006.01)

(52) U.S. Cl. .............................. 482/51; 601/34; 602/23

(58) Field of Classification Search .................. 482/74, 482/124; 601/34; 602/16, 23; 623/30, 31
See application file for complete search history.

(56) References Cited

U.S. PATENT DOCUMENTS 3,449,769 A * 6/1969 Mizen .......................... 623/26
4,422,453 A 12/1983 Salort
4,964,628 A * 10/1990 Poplawski .................... 482/51
5,020,837 A * 6/1991 Lin ........................ 292/169.13

(Continued)

FOREIGN PATENT DOCUMENTS

JP    58-41556    3/1983

(Continued)

*Primary Examiner*—Loan H Thanh
*Assistant Examiner*—Allana Lewin
(74) *Attorney, Agent, or Firm*—Squire, Sanders & Dempsey, LLP

(57) ABSTRACT

In order to provide a walking assistance device that can improve the force transmission efficiency from the assisting force generator disposed at a position corresponding to a hip joint to the leg while reducing the load upon the user's body, there is provided a walking assistance device comprising an assisting force generator (hip joint actuator 10) disposed at least on a side of a hip joint to provide an assisting force to a movement of a lower limb, comprising: a hip support member (1) for securely mounting the assisting force generator on the side of the hip joint; a lower leg support member (2) worn on a lower leg portion; and a force transmitting member (link bar 25) connecting the assisting force generator and the lower leg support member. In this way, the torque around the hip joint generated by the assisting force generator can be transmitted to the parts lower than the knee, and this can reduce an amount of force applied to the point of application of force on the body compared with the case where the torque is applied directly upon the thigh.

6 Claims, 6 Drawing Sheets

U.S. PATENT DOCUMENTS

| | | | | |
|---|---|---|---|---|
| 5,476,441 A | * | 12/1995 | Durfee et al. | 602/23 |
| 5,743,837 A | * | 4/1998 | Dias et al. | 482/124 |
| 6,589,195 B1 | * | 7/2003 | Schwenn et al. | 602/23 |
| 7,153,242 B2 | * | 12/2006 | Goffer | 482/66 |

FOREIGN PATENT DOCUMENTS

| | | |
|---|---|---|
| JP | 58-163364 | 9/1983 |
| JP | 61-228854 | 10/1986 |
| JP | 7-163607 | 6/1995 |
| JP | 9-103443 | 4/1997 |
| JP | 11-290360 | 10/1999 |
| JP | 2001-214303 | 8/2001 |

* cited by examiner

WALKING ASSISTANCE DEVICE

TECHNICAL FIELD

The present invention relates to a walking assistance device for mainly providing an assisting force to the movement of the hip joint.

BACKGROUND ART

Various proposals have been made for a walking assistance device that is adapted to mount an actuator to the hip joint or knee joint of a person having a walking impediment due to injury, disease or weakened muscle resulting from aging, so that the power from the actuator can be used to assist the movement of the lower limb.

Conventionally, in such a walking assistance device, a rotational force generated by an actuator secured on a support member fastened on the hip portion is transmitted to a support member fastened on the thigh to swing the thigh forward or backward around the hip joint to thereby provide the lower limb with a movement for stepping forward or backward.

However, in the prior art devices, such as those disclosed in Japanese Patent Application Laid-Open Publication No. 58-163364 (FIGS. 1-4) or Japanese Patent Application Laid-Open Publication No. 7-163607 (FIG. 1), when the drive torque from the actuator is applied to the thigh, the force applied to the thigh and hence the load upon the body tends to become undesirably large because a sufficient distance between the torque center and the point of application of force cannot be obtained. Further, because there is a big muscle in the thigh, the support member worn on the thigh tends to move easily even if the support member is fastened with quite a large tightening force, and this can lower the efficiency of transmission of force generated by the actuator.

DISCLOSURE OF THE INVENTION

In view of such problems of the prior art, a primary object of the present invention is to provide a walking assistance device that can improve the force transmission efficiency from the assisting force generator disposed at a position corresponding to a hip joint to the leg while reducing the load upon the user's body.

According to the present invention, such objects can be accomplished by providing a walking assistance device equipped with an assisting force generator (hip joint actuator 10) disposed at least on a side of a hip joint to provide an assisting force to a movement of a lower limb, comprising: a hip support member (1) for securely mounting the assisting force generator on the side of the hip joint; a lower leg support member (2) worn on a lower leg portion; and a force transmitting member (link bar 25) connecting the assisting force generator and the lower leg support member.

In this way, the torque around the hip joint generated by the assisting force generator can be transmitted to the parts lower than the knee, and this can reduce an amount of force applied to the point of application of force on the body compared with the case where the torque is applied directly upon the thigh.

Preferably, the hip support member is adapted to engage a region extending from a lower abdominal portion around a lower part of an abdominal muscle through right and left iliac crests to a backside of a sacroiliac joint. In this way, the torque around the hip joint can be supported by the whole hip portion and the reaction force imposed upon the body can be distributed to reduce the burden on the user. Also, because no part of the support member is attached on the thigh where an amount of muscle movement is large, the support member can be made less likely to move out of place.

Particularly, it is preferable that at least part (band-like member 24) of the lower leg support member is fitted on a portion between a lower part of a calf muscle and an upper part of an Achilles tendon. This allows the support member to engage a portion of the body where there is only a small amount of muscle movement and therefore, the support member can be made less likely to move out of place and the efficiency of force transmission to the lower leg portion can be improved.

Further, taking into account the dynamics of a human body, weights of the hip support member, the force transmitting member and the lower leg support member are decreased in this order in a similar fashion as in the human body structure. This can minimize the inertial mass and thus allow a more compact drive force generator to be used. Further, it can be avoided to apply an excessive force imposed upon the support member and this can reduce the burden on the wearer and improve the durability of the walking assistance device.

BEST MODE FOR CARRYING OUT THE INVENTION

Figure 1:
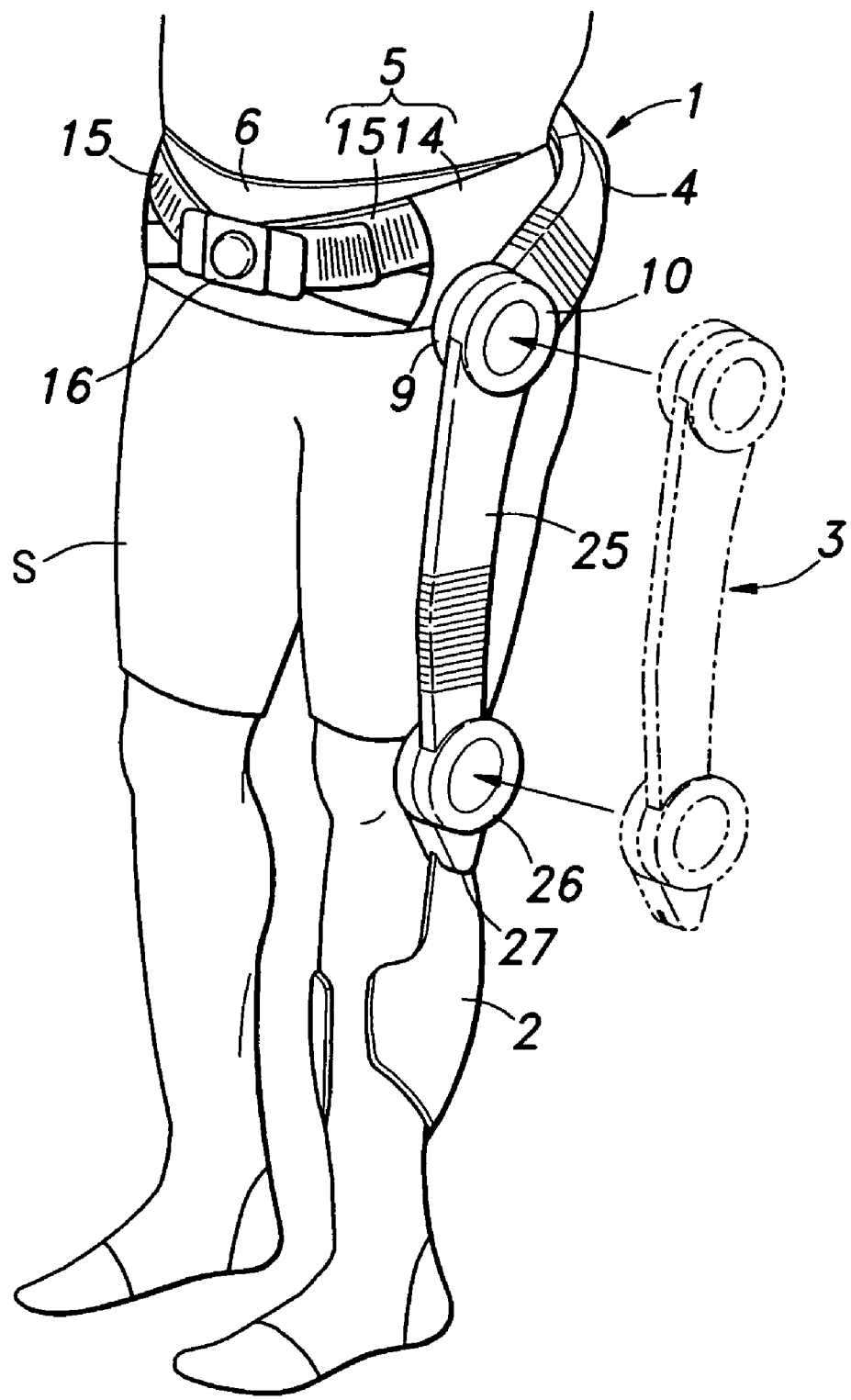
FIG. 1 is a perspective view showing a lower body on which a walking assistance device of the present invention is fitted.

FIG. 1 shows a walking assistance device of the present invention as worn on a user's body. The walking assistance device consists of a hip support member 1, lower leg support member 2 and a drive unit 3, where the hip support member 1 and the lower leg support member 2 are secured on a lower limb and a rotational torque generated by the drive unit 3 is transmitted to the lower limb via the hip and lower leg support members, to whereby provide a force for supplementing a reduced muscle power.

Figure 2:
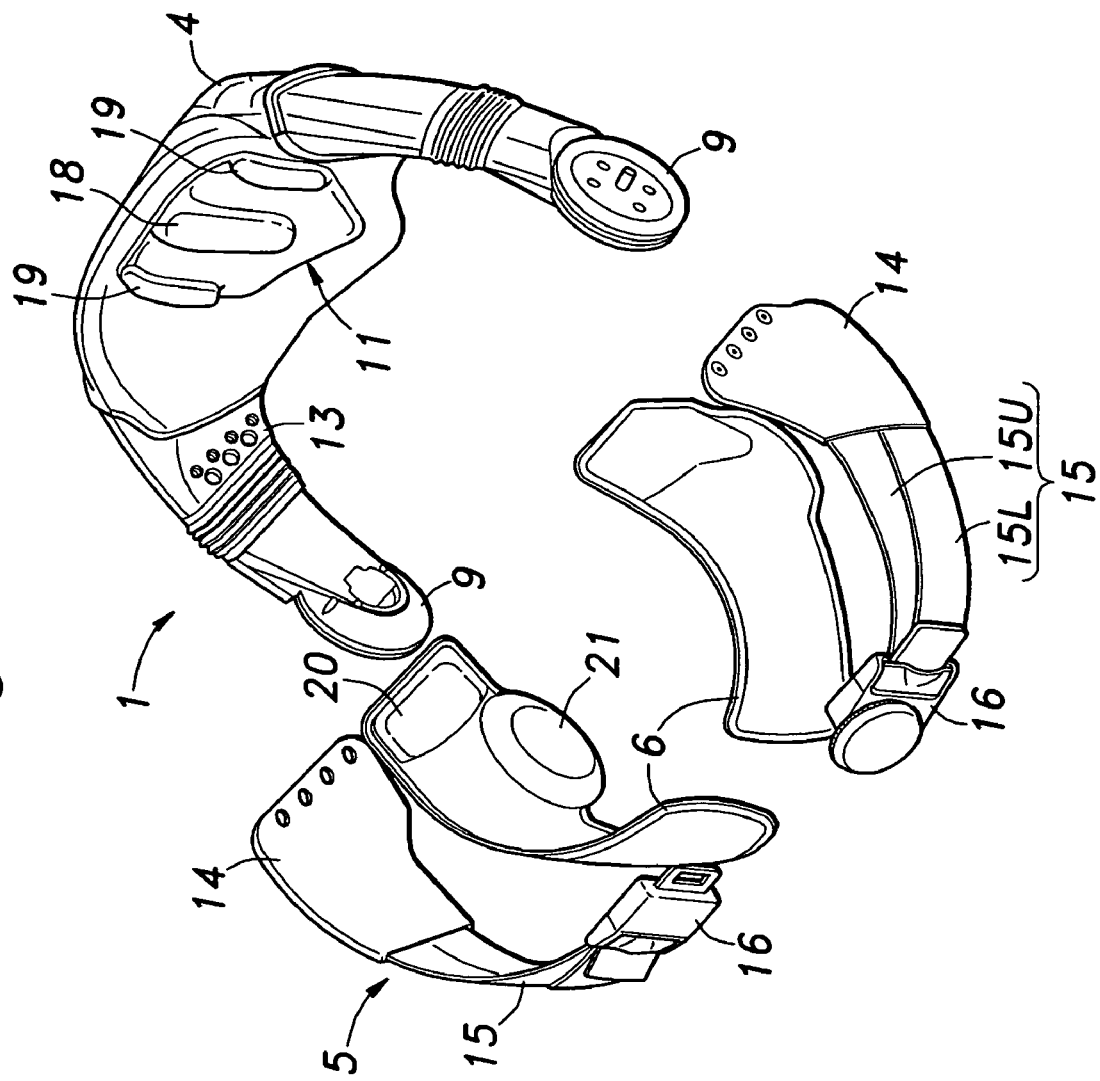
FIG. 2 is an exploded perspective view showing the structure of a hip support member of the walking assistance device according to the present invention.

The hip support member 1 comprises a back support 4, belt portion 5 and lining portion 6, as shown in FIG. 2.

Figure 3:
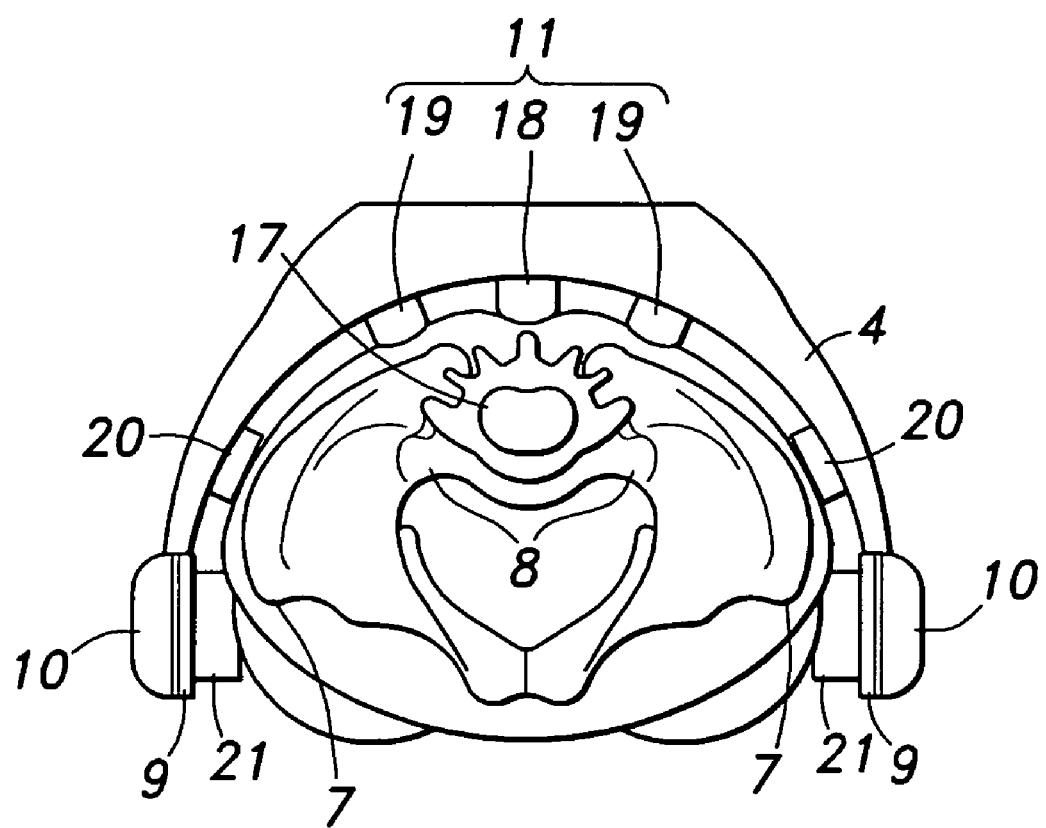
FIG. 3 is an explanatory drawing showing the relationship between a back support and the user's body.

Additionally referring to FIG. 3, the back support 4 is substantially of the shape of letter-U as seen in plan view so that it abuts a region of the body extending from right and left iliac crests (front ends of the pelvic bone) 7 to the backside of the sacroiliac joint (joint between the vertebrae and pelvic bone) 8, and consists of a substantially rigid body so as to withstand the drive force generated by a hip joint actuator 10, which consists of an electric motor equipped with a reduction gear and is mounted on a hip drive source mount 9 provided at each of the right and left ends of the back support 4. A rear portion of the back support 4 has a hollow space so that a control circuit and a battery for supplying electric power to the control circuit as well as to the electric motor are accommodated therein, though not explicitly shown in the drawings.

Further, at a portion of the back support 4 that directly abuts the user's body is provided a cushioning pad 11.

The belt portion 5 is made of a relatively rigid material and comprises: a pair of right and left bases 14 integrally attached by means of bolts to inner sides of belt joints 13 provided at right and left side portions of the back support 4; a pair of right and left web parts 15 fixed to front ends of the bases 14; and a pair of right and left buckles 16 attached to front ends of the web parts 15. The inner surface of the belt portion 5, i.e., the surface facing the hip portion of the user's body, is adapted to be attached with the lining portion 6 for protection by means of loop and hook fastener or the like.

The cushioning pad 11 provided to the back support 4 comprises a center pad 18 abutting a depression extending along a lumbar vertebra 17 and a pair of side pads 19 abutting laterally outer regions of erector spinae muscles slightly jutting out backward at right and left of the lumbar vertebra 17. Further, the lining portion 6 comprises iliac pads 20 abutting the iliac crests 7. Thus, a total of five pads abut principal portions of the hip to keep the back support 4 from moving out of place. Further, because direct contact of the hip drive source mount 9 with the user's body would cause pain to the user and could impart a large impact on the body if the user happens to fall, hip joint pads 21 are provided to the lining portion 6 so as to be interposed between the user's body and the hip drive source mount 9 and reduce the impact and pain.

Each of the web parts 15 comprises a pair of upper and lower plain weave belts secured to the associated base 14, and the front ends of the belts are joined together and attached to the corresponding buckle 16 so that they form a shape of letter-V that converges in the front direction. The upper belt 15U of each web part 15 extends from the joint with the base 14 disposed at a position corresponding to the iliac crest 7 toward the buckle 16 disposed at an intermediate portion ("tanden") between the navel and pubic bone along a direction of the extension of muscle fibers of the abdominal external oblique muscle. The lower belt 15L of the web part 15 extends from the joint with the base 14 disposed on a side of the hip joint toward the buckle 16 along a direction of fibers of the abdominal internal oblique muscle.

The upright posture of the spine is maintained by the balance of back muscle, pectoral muscle and abdominal muscle. The weakening of muscles of a person having walking impediment applies not only to the muscles of lower limb but also to the back, pectoral or abdominal muscles. Particularly, the weakening of the abdominal muscle can lower the abdominal cavity and cause the spine to bend in the shape of letter-S as seen in side view, thus making it difficult to maintain the upright posture during walking. According to the device of the present invention, the buckle 16 is positioned at a center of lower abdomen called "tanden" where the rectus abdominis muscle, abdominal external oblique muscle, abdominal internal oblique muscle, transversus abdominis muscle, etc. which play an important role in keeping the upright posture, overlap each other, and a tightening force is applied to the web parts 15 so that the back support 4 fitted on a region extending from the right and left iliac crests 7 to the backside of the secroiliac joint functions to correct the curve of the spine and stabilize the pelvis to achieve a proper posture and at the same time increase the abdominal cavity pressure to lift up the viscera to proper positions. Further, because the web parts 15 abut the lower abdominal portion with a relatively large contact area, the pressure applied to the abdominal cavity can be distributed evenly over the whole lower abdominal portion, thus reducing the uncomfortable pressure felt by the user.

Figure 4:
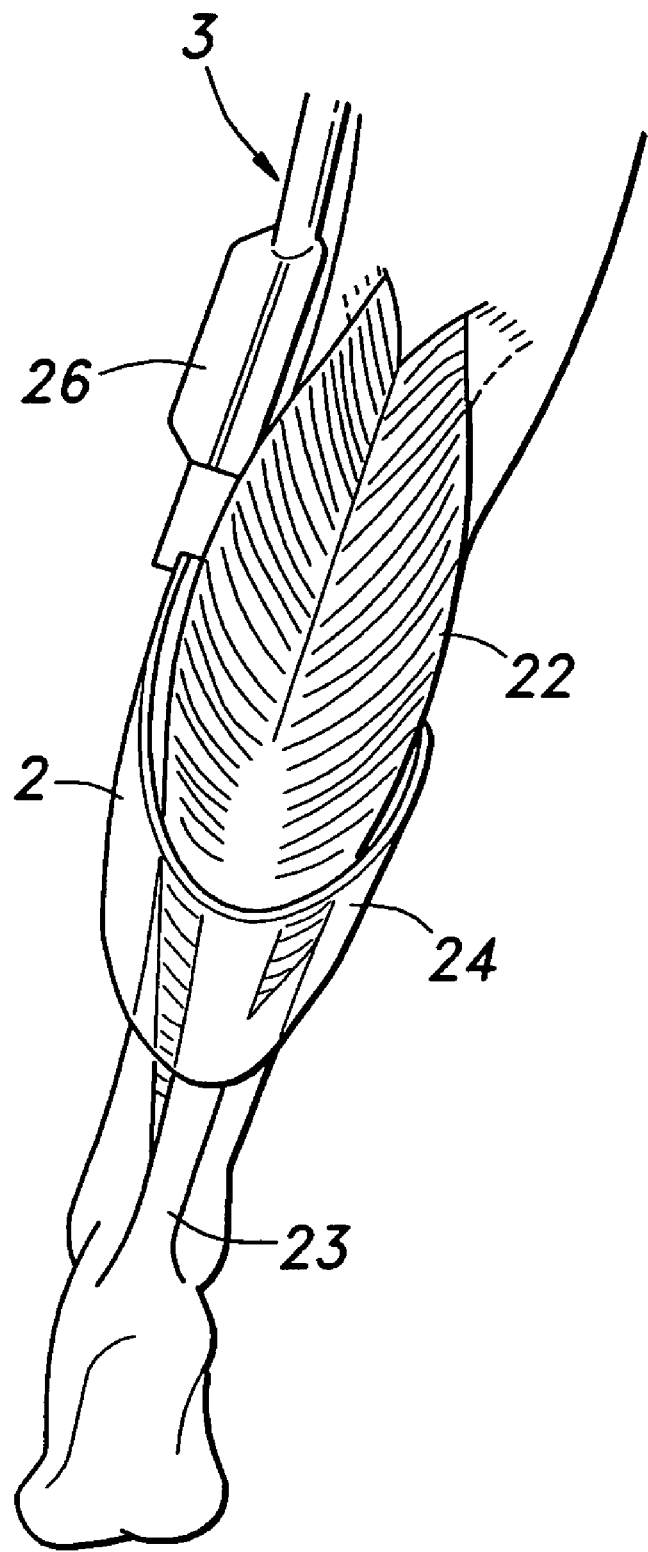
FIG. 4 is an explanatory drawing showing a lower leg support member fitted on a lower leg portion.

On the other hand, as also shown in FIG. 4, the lower leg support member 2 comprises a band-like member 24 wound around the region where the skin movement is relatively small during motion of the lower limb joints, i.e., region extending from lateral sides of an upper part of the anterior tibial muscle to the portion between a lower part of the calf muscle 22 and an upper part of the Achilles tendon 23. According to such a structure, it can be avoided to place the principal engagement points of the lower leg support member 2 on the calf, of which circumferential length can vary with the extension/flexion of the knee, or on the Achilles tendon where the skin moves with the motion of the ankle, and therefore it is possible to securely fasten the lower leg support member 2 on the lower leg with an abundant tightening force.

Figure 5:
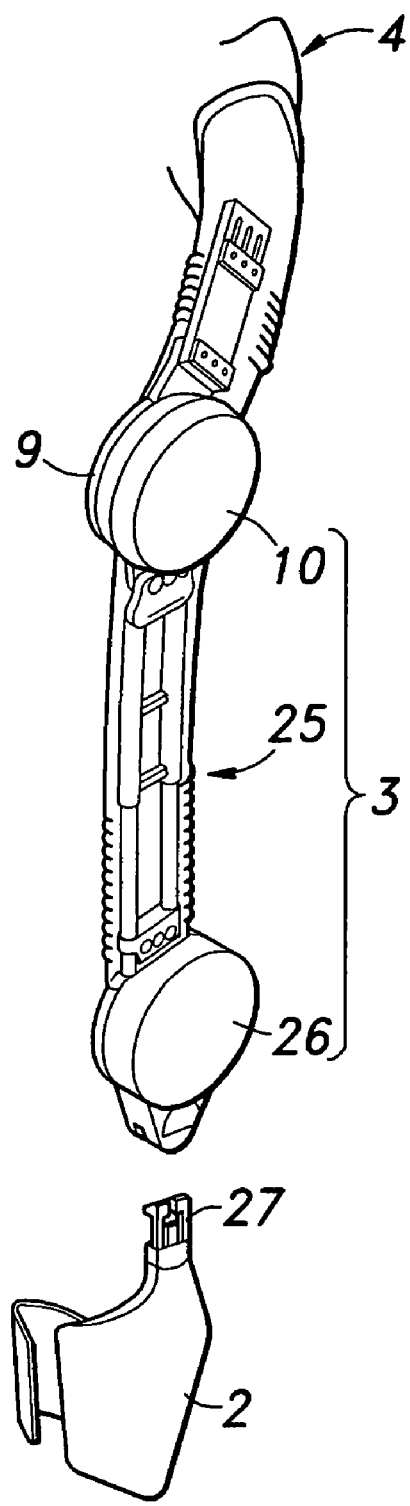
FIG. 5 is a perspective view of a principal part of the walking assistance device according to the present invention.

Additionally referring to FIG. 5, the drive unit 3 comprises a hip joint actuator 10 and a knee joint actuator 26, each consisting of an electric motor equipped with a reduction gear, where the actuators are attached to either end of a link bar 25 which is expandable and contractable in a telescopic fashion and serves as a force transmitting member. The drive unit 3 is adapted so as to be detachable from the hip drive source mount 9 provided to the back support 4 at a position corresponding to a side of the hip joint as well as from a knee drive source mount 27 provided to the lower leg support member 2 at a position corresponding to a side of the knee joint.

Figure 6:
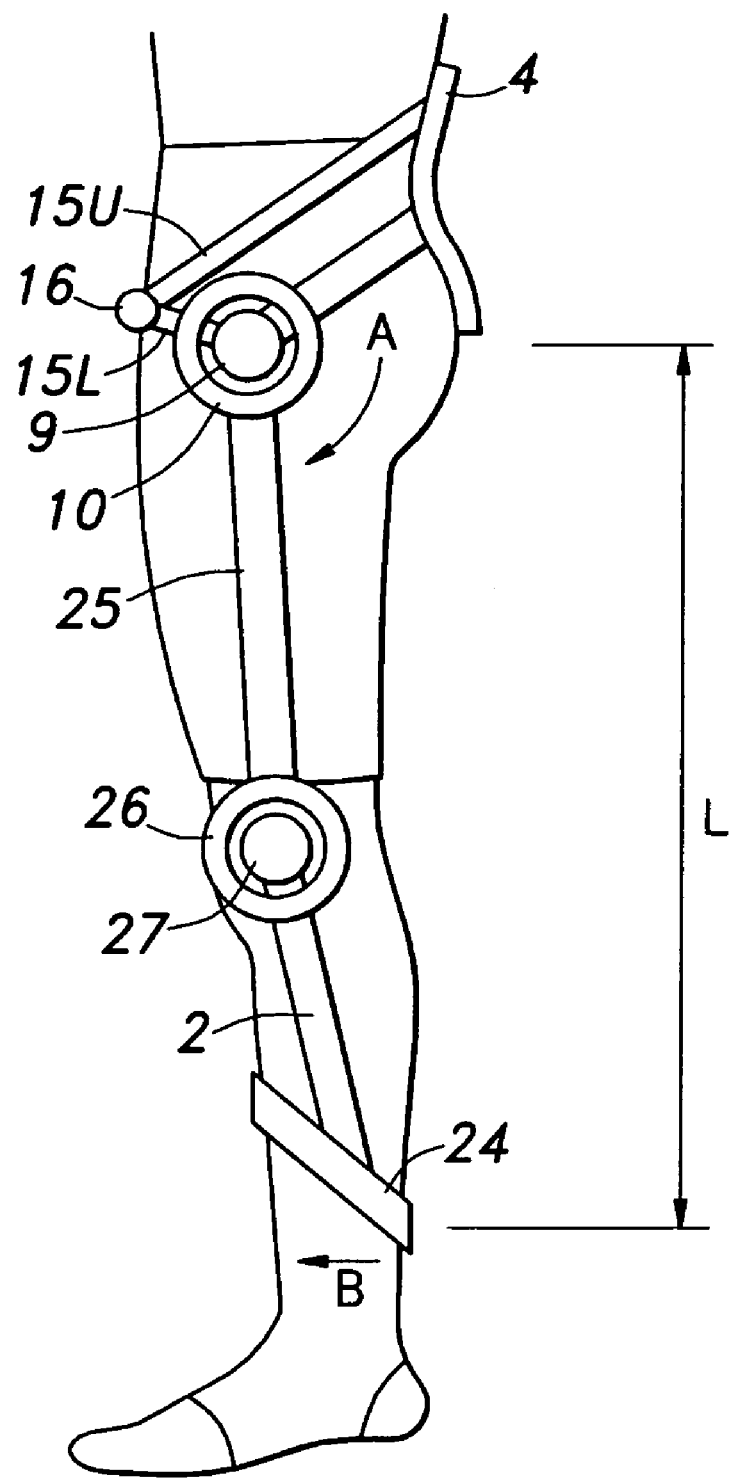
FIG. 6 is a side view schematically showing a lower body fitted with the device of the present invention.

In the above described walking assistance device of the present invention, the motion of stepping forward from the upright posture is carried out by rotating the hip joint actuator 10, the shaft of which is connected to the hip drive source mount 9, clockwise (arrow A) in FIG. 6 to thereby swing the link bar 25 integrally attached thereto. As the link bar 25 swings, the knee joint actuator 26 attached to a free end of the link bar 25 and the lower leg support member 2 connected to the knee joint actuator 26 via the knee drive source mount 27 are moved forward. Then the band-like member 24, which contacts a portion between a lower part of the calf muscle 22 and an upper part of the Achilles tendon where an amount of skin motion is relatively small, pushes the portion forward (arrow B), whereby an assisting force for moving the leg forward is provided to the lower limb. In this way, it is possible to maximize the distance (L) from the torque center of the hip joint actuator 10 to the point of application of force, and this can decrease the contact pressure of the band-like member 24 upon the portion between the lower part of the calf muscle 22 and the upper part of the Achilles tendon 23, to thereby reduce the discomfort to the user.

In the walking assistance device of the present invention, the weights of the hip support member 1 including the hip joint actuator 10, link bar 25 including the knee joint actuator 26, and lower leg support member 2 are determined so as to decrease in this order. In this way, a part having a larger rotation radius is provided with a smaller inertial mass, and this can minimize the consumption energy as well as the required drive force generated by the hip joint actuator, which can lead to a more compact assisting force generation unit 3. At the same time, this can improve power transmission efficiency and prevent excessive force from being applied to the component parts, which can lead to higher durability of the walking assistance device.

When a person walks, one leg is swung forward while the center of gravity is moved forward. During this motion, the hip joint actuator 10 and the knee joint actuator 26 can be operated in cooperation with each other to achieve smoother and more natural motion of the legs.

Regarding the extension and flexion movements of the knee joint, when the user crouches down, both of the actuators 10, 26 are rotated with an adequate damping force to support the weight of the upper body. When the user stands up, both of the actuators 10, 26 are rotated in the direction to extend the joints and lift up the upper body. Thus, by appropriately controlling the driving force and damping force of the actuators 10, 26, a favorable assisting operation for muscle expansion and contraction movements can be achieved.

If the device of the present invention is worn over a spat S for exercise that is adapted to provide a specific muscle(s) with a tightening force that is equivalent to that produced by taping (see Japanese Patent Application Laid-Open No. 2001-214303), the device can function even more effectively to improve the motion ability of the user in cooperation with the muscle support effect resulting from the tightening force produced by the fibers forming the spat S. Also, if the drive torque is effected in reverse, the device of the present invention can apply a load torque upon the joint, and therefore the device can be used not only as a motion assisting device but also as a load generator for medical treatment, rehabilitation or training for muscle development.

INDUSTRIAL APPLICABILITY

As described above, according to the present invention, the following advantages can be obtained:
1. Because the hip joint actuator secured on the side of the hip joint and the lower leg joint attached to the lower leg portion are connected by the connecting bar, the torque around the hip joint generated by the hip joint actuator can be transmitted to the parts lower than the knee, and this can reduce an amount of force applied to the point of application of force on the body compared with the case where the torque is applied directly upon the thigh.
2. Because the hip support member is adapted to engage a region extending from a lower abdominal portion around a lower part of an abdominal muscle through right and left iliac crests to a backside of a sacroiliac joint, the torque around the hip joint can be supported by the whole hip portion and the reaction force can be distributed all over the hip portion, and this can reduce the burden upon the user. Also, because no part of the support member is attached on the thigh where an amount of muscle movement is large, the support member can be made less likely to move out of place.
3. Because the band-like member of the lower leg support member is fitted on a portion between a lower part of the calf muscle and an upper part of the Achilles tendon, where there is only a small amount of muscle movement, the support member can be made less likely to move out of place and the efficiency of force transmission to the lower leg portion can be improved.
4. Because the weights of the hip support member, the force transmitting member and the lower leg support member are decreased in this order, the inertial mass can be minimized and a more compact drive force generator is allowed to be used. Further, it can be avoided to apply an excessive force imposed upon the support member and this can reduce the burden on the wearer and improve the durability of the walking assistance device.

The invention claimed is:

1. A walking assistance device comprising an assisting force generator disposed at least on a side of a hip joint to provide an assisting force to a movement of a lower limb, comprising:
   a hip support member for securely mounting the assisting force generator on the side of the hip joint;
   a lower leg support member worn on a lower leg portion excluding a foot; and
   a force transmitting member for transmitting a drive force from the assisting force generator only to the lower leg support member.

2. The walking assistance device according to claim 1, wherein the hip support member is configured to engage a region of a user's body, the region extending from a lower abdominal portion around a lower part of an abdominal muscle through right and left iliac crests to a backside of a sacroiliac joint.

3. The walking assistance device according to claim 1, wherein the hip support member weighs more than the force transmitting member, and the force transmitting member weighs more than the lower leg support member.

4. The walking assistance device according to claim 1, further comprising an additional assisting force generator disposed on a side of a knee of the lower limb, the additional assisting force generator being connected to the lower leg support member.

5. The walking assistance device according to claim 1, comprising a pair of said assisting force generators disposed on left and right sides of the hip joint, respectively.

6. A walking assistance device comprising an assisting force generator disposed at least on a side of a hip joint to provide an assisting force to a movement of a lower limb, comprising:
   a hip support member for securely mounting the assisting force generator on the side of the hip joint;
   a lower leg support member worn on a lower leg portion; and
   a force transmitting member for transmitting a drive force from the assisting force generator only to the lower leg support member,
   wherein the lower leg support member is fitted on a portion between a lower part of a calf muscle and an upper part of an Achilles tendon while avoiding the calf muscle and the Achilles tendon.

* * * * *